United States Patent [19]
Hirai et al.

[11] Patent Number: 4,523,037
[45] Date of Patent: Jun. 11, 1985

[54] PROCESS FOR SELECTIVELY PRODUCING PARA-SUBSTITUTED DERIVATIVES OF PHENOLS

[75] Inventors: Hidefumi Hirai; Makoto Komiyama, both of Tokyo, Japan

[73] Assignee: Asahi Kasei Kogyo Kabushiki Kaisha, Osaka, Japan

[21] Appl. No.: 530,157

[22] Filed: Sep. 7, 1983

Related U.S. Application Data

[63] Continuation-in-part of Ser. No. 385,405, filed as PCT JP 82/00066, Mar. 9, 1982, published as WO 82/03073 Sep. 16, 1982, § 102(e) date May 17, 1982, abandoned.

[30] Foreign Application Priority Data

Mar. 9, 1981 [JP] Japan ................................. 56-32542
Sep. 25, 1981 [JP] Japan ............................... 56-151571
Sep. 26, 1981 [JP] Japan ............................... 56-152524

[51] Int. Cl.$^3$ ............................................. C07C 5/393
[52] U.S. Cl. .................................... 568/442; 568/433; 568/377; 568/657; 568/813
[58] Field of Search ................ 562/475; 568/442, 433, 568/377, 657, 813

[56] References Cited

PUBLICATIONS

Ohara M. et al., Pharmazie, vol. 33, No. 7 (1978), p. 467.
Chemical Review, 60, 169 (1960).
J. Amer. Chem. Soc., 81, 6446 (1959).

Primary Examiner—Paul J. Killos
Attorney, Agent, or Firm—Sprung, Horn, Kramer & Woods

[57] ABSTRACT

By reacting, using as a catalyst a modified or unmodified cyclodextrin, a phenol compound with a haloform in the presence of an alkali metal hydroxide, while maintaining the molar ratio of the cyclodextrin to the haloform at 0.5 to 10, a substituent group derived from the haloform can be introduced to the para-position of the phenol compound with high selectivity, whereby useful para-substituted phenol derivatives can be advantageously obtained.

10 Claims, No Drawings

PROCESS FOR SELECTIVELY PRODUCING PARA-SUBSTITUTED DERIVATIVES OF PHENOLS

This application is a continuation-in-part of our U.S. patent application Ser. No. 385,405 filed as PCT JP 82/00066 Mar. 9, 1982, published as WO 82/03073 Sept. 16, 1982, § 102(e) date on May 17, 1982 now abandoned.

This invention relates to a process for selectively producing para-substituted derivatives of phenols. More particularly, the present invention is concerned with a process for producing para-substituted derivatives of phenols which comprises reacting a phenol compound with a haloform in the presence of an alkali metal hydroxide, using a cyclodextrin as a catalyst, while maintaining the molar ratio of the cyclodextrin to the haloform at 0.5 to 10, thereby to obtain the desired para-substituted derivative with an extremely high selectivity.

It is known that 2,5-cyclohexadienone derivatives having a dihalomethyl group at the 4-position or para-hydroxybenzaldehyde derivatives are prepared by reacting a phenol with a haloform under alkaline conditions. The products thus obtained are extremely valuable compounds as pharmaceuticals, agricultural chemicals, or raw materials for various physiologically active substances such as agricultural chemicals and pharmaceuticals, and dyes.

However, known reaction processes have serious disadvantages of extremely low selectivity and therefore poor yield. Accordingly, the known process cannot be advantageously used in practice.

For example, para-hydroxybenzaldehyde which, nowadays, is of increasing importance as an anticarcinogen or a raw material for pharmaceuticals, agricultural chemicals and dyes, has conventionally been synthesized by reacting phenol with chloroform in the presence of an alkali metal hydroxide. In the reaction, however, para-hydroxybenzaldehyde is obtained in a selectivity as low as about 30%, and a large amount of salicylaldehyde is formed as a by-product. Therefore, the production of para-hydroxybenzaldehyde in accordance with this process requires not only a large amount of raw materials but also an operation for separation.

2,4-Dihydroxybenzaldehyde, nowadays, is also of increasing importance in view of its interesting behaviors such as cancer-controlling effect, plant root growth-promoting effect, antibacterial effect and photophosphorylation-controlling effect in chloroplast. For the production of 2,4-dihydroxybenzaldehyde, known is a process in which 1,3-dihydroxybenzene is reacted with chloroform in the presence of an alkali metal hydroxide. However, in this known process, a large amount of 2,4-dihydroxy-3-formylbenzaldehyde is formed as a by-product, and 2,4-dihydroxybenzaldehyde which is the intended product is obtained only in low yield and with low selectivity. Accordingly, for producing 2,4-dihydroxybenzaldehyde by this process, not only large amounts of raw materials but also an operation for separation is required.

2,5-Cyclohexadienone derivatives are highly reactive due to the conjugation of two C-C double bonds with a carbonyl group, and therefore are valuable as raw materials for the syntheses of physiologically active substances and other useful substances. Moreover, many of 2,5-cyclohexadienone derivatives themselves have physiological activities. Hitherto is known the Reimer-Tiemann reaction in which a para-substituted phenol is reacted with a haloform and sodium hydroxide or potassium hydroxide to give a 4-dihalomethyl-2,5-cyclohexadienone derivative. The reaction, however, gives compounds having substituents introduced mainly to the ortho-position. Therefore, the conventional process gives 2,5-cyclohexadienone derivatives in an yield as low as 5 to 10%, and requires not only large amounts of raw materials, but also a complicated operation for separation.

In Pharmazie, Vol. 33, 467 (1978), it was reported that by the addition of β-cyclodextrin to a reaction system comprising phenol, chloroform and an alkali metal hydroxide the selectivity for formation of para-hydroxybenzaldehyde is improved. However, in such a reaction, since all the amount of chloroform is added at the time of initiation of the reaction, it is required to add the β-cyclodextrin in an amount of 0.75 in terms of molar ratio with respect to the phenol in order to attain a conversion of 19% and selectivity of 95%.

As described above, any of the conventional processes for introducing a substituent derived from a haloform to the para-position of phenols are unsatisfactory from a practical point of view because of low selectivity.

The present inventors have made extensive and intensive studies to develop a process in which a substituent derived from a haloform is introduced to the 4-position of phenols with high selectivity to give intermediates for the production of various useful substances as mentioned above. As a result, it has been found that, when a phenol compound is reacted with a haloform in the presence of a cyclodextrin under an alkaline condition while maintaining the molar ratio of the cyclodextrin to the haloform at 0.5 to 10, a substituent group derived from the haloform is introduced to the 4-position of the phenol compound with high selectivity, and therefore the intended para-substituted phenol derivative can be obtained in high yield. Based on such a novel finding, the present invention has been made.

Accordingly, it is an object of the present invention to provide a process for producing a para-substituted phenol derivative with high selectivity.

The foregoing and other objects, features and advantages of the present invention will be apparent to those skilled in the art from the following detailed description and appended claims.

According to the present invention, there is provided a process for producing a para-substituted phenol derivative which comprises reacting a phenol compound represented by the formula (I)

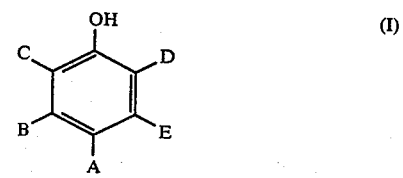

wherein A, B, C, D and E each independently stand for hydrogen, a hydroxyl group, a substituted or unsubstituted alkyl group, a substituted or unsubstituted allyl group, a substituted or unsubstituted alkoxyl group or a substituted or unsubstituted aryl group, provided that A does not stand for a hydroxyl group and that when two or more of A, B, C, D, and E each independently stand for a substituted or unsubstituted alkyl group or a substituted or unsubstituted alkoxyl group, they have their respective free terminal ends or at least one of them is bonded to another group selected from said alkyl and alkoxyl groups to form a ring, with a haloform in the presence of an alkali metal hydroxide, using as a catalyst a modified or unmodified cyclodextrin, while maintaining the molar ratio of the modified or unmodified cyclodextrin to the organic halide at 0.5 to 10, thereby to selectively introduce an aldehyde group or dihalomethyl group derived from said haloform to the para-position of the phenol compound.

By the term "phenol compound" as used herein is meant phenol(hydroxybenzene) or its derivative which is defined by the above-mentioned formula (I). The substituted or unsubstituted alkyl group, the substituted or unsubstituted allyl group, the substituted or unsubstituted alkoxyl group and the substituted or unsubstituted aryl group each may preferably have carbon atoms of not more than 6 with respect to the substituents B, C, D and E, and each may preferably have carbon atoms of not more than 12 with respect to the substituent A.

As the substituent to be introduced to the alkyl group, allyl group, alkoxyl group and aryl group, there can be mentioned an alkyl group, a halogen atom and others without specific restriction. However, too large a group is undesired.

The haloform may be used in an amount of 1 to 20 mols, preferably 1.5 to 10 mols per mol of the phenol compound used.

The alkali metal hydroxide to be used in the process of the present invention may preferably be sodium hydroxide or potassium hydroxide. The alkali metal hydroxide may be used in a stoichiometrical amount relative to the phenol compound. Usually, however, 1 to 15 times, preferably 1.5 to 10 times the stoichiometrical amount of the alkali metal hydroxide may be used taking into consideration of the rate of reaction and the like.

The reaction according to the process of the present invention is usually carried out in a reaction medium. As the reaction medium, there is employed an aqueous solvent, preferably water, because of the requirement that the reaction medium be capable of dissolving the alkali metal hydroxide therein. There may also be used, as the reaction medium, a mixture of water with a small amount of an organic solvent which is soluble in water and can be present stably under the reaction conditions. Examples of such an organic solvent include methanol, ethanol, acetone, dimethoxyethane and the like. The concentration of the alkali metal hydroxide in the reaction solvent may be in the range of 5 to 20% by weight, preferably 10 to 15% by weight.

A modified or unmodified cyclodextrin is used as a catalyst in the process of the present invention. Any of modified or unmodified α-, β- and γ-cyclodextrins may be used. Usually, satisfactory results can be obtained by the use of unmodified α-, β- or γ-cyclodextrin. However, a more improved yield and selectivity in the reaction are achieved by the use of a modified α-, β- or γ-cyclodextrin of which the primary hydroxyl groups, for example, are all or partly substituted with a group which is stable under alkaline conditions, such as a N-methylformamido group. The above-mentioned modified cyclodextrin may be prepared according to the method described in J. Amer. Chem. Soc., 102, 762 (1980).

It is essential to the process of the present invention that the reaction of a phenol compound and a haloform be effected while maintaining the molar ratio of the cyclodextrin to the haloform in the reaction system at 0.5 to 10, preferably 0.8 to 5. The process of the present invention can be practiced by intermittently or gradually adding a haloform to a system comprising a phenol compound, a cyclodextrin and an alkali metal hydroxide. In this connection, the control of the molar ratio of the cyclodextrin to the haloform in the system may be made by the following method. At a predetermined time interval during the course of the reaction, part of the reaction mixture is taken, subjected to the determination of haloform contained therein by gas chromatography, and the rate of the addition of the haloform to the system is adjusted so that the molar ratio of the cyclodextrin to the haloform is maintained at a value falling within the range as mentioned above. The amount of the cyclodextrin relative to the amount of the phenol compound used is not critical as far as the molar ratio of the cyclodextrin to the haloform in the system and the molar ratio of the haloform to the phenol compound are within the ranges as mentioned above. But, in general, the cyclodextrin may be used in an amount of 0.00001 to 0.7, preferably 0.01 to 0.5 in terms of molar ratio with respect to the phenol compound used.

The reaction temperature is not critical, and may be suitably determined according to a phenol compound to be used, but generally is 0° to 120° C., preferably 20° to 100° C., more preferably 50° to 80° C.

The reaction time is also not critical, and may be suitably determined according to a phenol compound to be used, the amounts of reactants, reaction temperature, manner of addition of reactants and the like, but generally is 10 minutes to 20 hours.

The reaction pressure is also not restricted, and the reaction is usually carried out at atmospheric pressure from a viewpoint of ease in operation.

By the reaction of a phenol compound with a haloform according to the process of the present invention, there is produced a para-substituted phenol derivative of the kind varied depending on the kinds of the phenol compound as described later.

From phenol compounds of the formula (I) in which A is a hydrogen atom, para-hydroxybenzaldehydes are obtained.

From phenol compounds of the formula (I) in which A is other substituent than hydrogen, namely, a substituted or unsubstituted alkyl group, a substituted or unsubstituted allyl group, a substituted or unsubstituted alkoxyl group or a substituted or unsubstituted aryl group, there are obtained 4-dihalomethyl-2,5-cyclohexadienone derivatives. Illustratively stated, when A in the formula (I) is hydrogen, there is obtained a para-substituted phenol deviative represented by the formula (II)

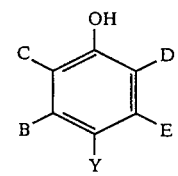

(II)

wherein B, C, D and E are as defined above and Y stands for an aldehyde group, whereas when A in the formula (I) is a substituted or unsubstituted alkyl group, a substituted or unsubstituted allyl group, a substituted or unsubstituted alkoxyl group or a substituted or unsubstituted aryl group, there is obtained a para-substituted phenol derivative represented by the formula (III)

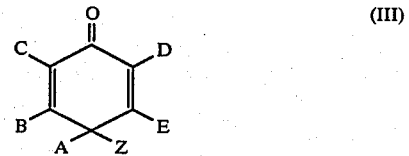

wherein A, B, C, D and E are as defined above, provided that A does not stand for hydrogen, and Z stands for haloform residue.

As is apparent from the foregoing, according to the process of the present invention, a variety of useful phenol derivatives having a substituent introduced to the para-position thereof are produced from phenols with high selectivity. Therefore, not only can be reduced the required amounts of phenols as raw materials but also the purification process can be extremely simplified, thus enabling the production process of the desired products to be economic.

The present invention will be illustrated in more detail with reference to the following Examples. Unless otherwise specified, reactions were carried out at atmospheric pressure in Examples and Comparative Examples as will be described hereinafter.

In Examples and Comparative Examples, the yield of and the selectivity for a produced para-substituted phenol derivative are respectively those obtained by the following formulae:

Yield of a para-substituted phenol derivative (%) = (1)

$$\frac{\text{mole number of produced para-substituted phenol derivative}}{\text{mole number of fed phenol}} \times 100$$

Selectivity for a para-substituted phenol derivative (%) = (2)

$$\frac{\text{mole number of produced para-substituted phenol derivative}}{\left(\begin{array}{c}\text{mole number of}\\\text{produced ortho-}\\\text{substituted}\\\text{phenol derivative}\end{array}\right) + \left(\begin{array}{c}\text{mole number of}\\\text{produced para-}\\\text{substituted}\\\text{phenol derivative}\end{array}\right)} \times 100$$

In Examples and Comparative Examples, there was produced no meta-substituted phenol derivative.

EXAMPLE 1

In 50 ml of an aqueous 10% sodium hydroxide solution were dissolved 1.0 g (10.6 mmol) of phenol (first class grade reagent, manufactured and sold by Koso Chemical Co., Ltd., Japan) and 2.2 g (2.1 mmol) of α-cyclodextrin (special grade reagent, manufactured and sold by Nakarai Chemical Ltd., Japan). The resulting solution was heated to 60° C. while agitating by means of a magnetic stirrer. Then, 3 ml (37.4 mmol) of chloroform (special grade reagent, manufactured and sold by Tokyo Kasei Co., Ltd., Japan) was gradually added to the resulting solution heated at 60° C. so that the reaction of phenol with chloroform was effected while maintaining the molar ratio of α-cyclodextrin to chloroform in the solution at 0.9 to 1.6. The reaction was continued at 60° C. for 10 hours. The control of the molar ratio of α-cyclodextrin to chloroform in the reaction system was effected as follows. Every two hours during the course of the reaction, part of the reaction mixture was taken and subjected to the determination of chloroform contained therein by means of 701-type Gas Chromatograph manufactured by Ohkura Rikagaku Kenkyusho Co., Ltd., Japan (packing material, Porapak Q manufactured and sold by Gasukuro Kogyo Inc., Japan; column length, 2 m; column temperature, 30° C.; carrier gas, helium), and the rate of the addition of chloroform to the reaction system was adjusted so that the molar ratio of α-cyclodextrin to chloroform in the reaction system was maintained at 0.9 to 1.6.

After completion of the reaction, the reaction mixture was acidified with hydrochloric acid, and subjected to extractions each with 50 ml of ethyl ether 5 times. The ethyl ether layer was washed with water, and then evaporated to dryness, thereby to obtain 1.1 g of a solid. The solid thus obtained was treated with benzene to give 0.6 g of a benzene-insoluble matter and 0.5 g of a benzene-soluble matter. The infrared spectrum of the benzene-insoluble matter was in agreement with that of para-hydroxybezaldehyde (special grade reagent, manufactured by Tokyo Kasei Co., Ltd., Japan). On the other hand, the spectrum of the benzene-soluble matter was in agreement with that of phenol. Salicylaldehyde was observed neither in the benzene-soluble matter nor in the benzene-insoluble matter. The yield of the intended product was 46% and the selectivity was 100%.

In this example, α-cyclodextrin was used in an amount of 0.2 in terms of molar ratio with respect to the phenol.

COMPARATIVE EXAMPLE 1

Substantially the same procedures as in Example 1 were repeated except that the use of 2.2 g of α-cyclodextrin was omitted. After completion of the reaction, the reaction mixture was acidified with hydrochloric acid, and subjected to extractions each with 50 ml of ethyl ether 5 times. The ethyl ether layer was washed with water, and then evaporated, thereby to obtain 1.0 g of an oily material. The oily material thus obtained was analyzed by means of 701-type Gas Chromatograph manufactured by Ohkura Rikagaku Kenkyusho Co., Ltd., Japan (packing material, Uniport HP manufactured and sold by Gasukuro Kogyo Inc., Japan; column length, 2 m; column temperature, 140° C.; carrier gas, helium). The analysis showed that the oily material was a mixture of 0.2 g (1.6 mmol) of para-hydroxybenzaldehyde, 0.4 g (3.2 mmol) of salicylaldehyde and 0.4 g of phenol. Namely, the yield of the intended product was 15% and the selectivity was 33%.

COMPARATIVE EXAMPLE 2

In 50 ml of an aqueous 10% sodium hydroxide solution were dissolved 1.0 g (10.6 mmol) of phenol (first class grade reagent, manufactured and sold by Koso Chemical Co., Ltd., Japan) and 2.2 g (2.1 mmol) of α-cyclodextrin (special grade reagent, manufactured and sold by Nakarai Chemical Ltd., Japan). To the resulting solution was added 3 ml (37.4 mmol) of chloroform (special grade reagent, manufactured and sold by Tokyo Kasei Co., Ltd., Japan). Namely, the molar ratio of α-cyclodextrin to chloroform was 0.06 at the start of the reaction. The solution was heated at 60° C. for 10 hours while agitating by means of a magnetic stirrer. After completion of the reaction, the reaction mixture was acidified with hydrochloric acid, and subjected to extractions each with 50 ml of ethyl ether 5 times. The ethyl ether layer was washed with water, and then evaporated, thereby to obtain 1.1 g of an oily material. The oily material thus obtained was analyzed by means of 701-type Gas Chromatograph manufactured by Ohkura Rikagaku Kenkyusho Co., Ltd., Japan (packing material, Uniport HP manufactured and sold by Gasukuro Kogyo Inc., Japan; column length, 2 m; column temperature, 140° C.; carrier gas, helium). The analysis showed that the oily material was a mixture of 0.4 g (3.2 mmol) of para-hydroxybenzaldehyde, 0.3 g (2.4 mmol) of salicylaldehyde and 0.4 g of phenol. Namely, the yield of the intended product was 30% and the selectivity was 57%.

In this example α-cyclodextrin was used in an amount of 0.2 in terms of molar ratio with respect to the phenol, which was the same as in Example 1.

EXAMPLE 2

Substantially the same procedures as in Example 1 were repeated except that 2.4 g (2.1 mmol) of β-cyclodextrin (special grade reagent, manufactured and sold by Nakarai Chemical Ltd., Japan) was used instead of 2.2 g of α-cyclodextrin. There was obtained 0.5 g (4.0 mmol) of para-hydroxybenzaldehyde, with 0.6 g of unreacted phenol recovered. Salicylaldehyde was not detected. Namely, the yield of the intended product was 39% and the selectivity was 100%.

In this example, β-cyclodextrin was used in an amount of 0.2 in terms of molar ratio with respect to the phenol.

COMPARATIVE EXAMPLE 3

Substantially the same procedures as in Comparative Example 2 were repeated except that 2.4 g (2.1 mmol) of β-cyclodextrin (special grade reagent, manufactured and sold by Nakarai Chemical Ltd., Japan) was used instead of 2.2 g of α-cyclodextrin. Namely, the molar ratio of β-cyclodextrin to chloroform was 0.06 at the start of the reaction. There was obtained a mixture of 0.3 g (2.4 mmol) of para-hydroxybenzaldehyde, 0.2 g (1.6 mmol) of salicylaldehyde and 0.5 g of phenol. Namely, the yield of the intended product was 23% and the selectivity was 60%.

In this example, β-cyclodextrin was used in an amount of 0.2 in terms of molar ratio with respect to the phenol, which was the same as in Example 2.

EXAMPLE 3

In 60 ml of an aqueous 10% sodium hydroxide solution were dissolved 1.0 g (9.1 mmol) of 1,3-dihydroxybenzene (special grade reagent, manufactured and sold by Tokyo Kasei Co., Ltd., Japan) and 3.0 g (2.6 mmol) of β-cyclodextrin (special grade reagent, manufactured and sold by Nakarai Chemical Ltd., Japan). Then, 5 ml (62.3 mmol) of chloroform (special grade reagent, manufactured and sold by Tokyo Kasei Co., Ltd., Japan) was gradually added to the resulting solution heated at 60° C. so that the reaction of phenol with chloroform was effected while maintaining the molar ratio of β-cyclodextrin to chloroform in the solution at 0.8 to 2.0. The reaction was continued at 60° C. for 7 hours.

After completion of the reaction, the reaction mixture was acidified with hydrochloric acid and subjected to extractions each with 50 ml of ethyl ether 3 times. The ethyl ether layer was washed with water, and then dried, thereby to obtain 1.1 g of a product. The product thus obtained was analyzed by means of 701-type Gas Chromatograph manufactured by Ohkura Rikagaku Kenkyusho Co., Ltd., Japan (packing material, Tenax GC manufactured and sold by Gasukuro Kogyo Inc., Japan; column length, 2 m; column temperature, 300° C.; carrier gas, helium). The analysis showed that the product was entirely 2,4-dihydroxybenzaldehyde, without any 2,4-dihydroxy-3-formylbenzaldehyde detected. namely, the yield of the intended product was 88% and the selectivity was 100%.

COMPARATUVE EXAMPLE 4

Substantially the same procedures as in Example 3 were repeated except that the use of 8.0 g of β-cyclodextrin was omitted.

After completion of the reaction, the reaction mixture was acidified with hydrochloric acid, and subjected to extractions each with 50 ml of ethyl ether 3 times. The ethyl ether layer was washed with water, and then dried, thereby to obtain 1.1 g of a product. The product thus obtained was analyzed by means of 701-type Gas Chromatograph manufactured by Ohkura Rikagaku Kenkyusho Co., Ltd., Japan. The analysis showed that the product was a mixture of 0.4 g of 2,4-dihydroxybenzaldehyde and 0.7 g of 2,4-dihydroxy-3-formylbenzaldehyde. Namely, the yield of the intended product was 32% and the selectivity was 36%.

EXAMPLE 4

In 50 ml of an aqueous 10% sodium hydroxide solution were dissolved 1 g of p-cresol and 3 g of β-cyclodextrin. To the resulting solution, 5 ml of chloroform was gradually added at 75° C. so that the reaction of phenol with chloroform was effected while maintaining the molar ratio of β-cyclodextrin to chloroform in the solution at 0.8 to 2.0. The reaction was continued at 75° C. for 15 hours. The control of the molar ratio of β-cyclodextrin to chloroform in the reaction system was effected in the same manner as in Example 1. After completion of the reaction, the reaction mixture was subjected to extractions each with 50 ml of chloroform 5 times, and then the chloroform layer was dried, thereby to obtain 0.68 g of a product. The $^1$H-NMR measurement showed that the product thus obtained was entirely 4-dichloromethyl-4-methyl-2,5-cyclohexadienone. Namely, the yield of the intended product was 39% and the selectivity was 100%.

COMPARATIVE EXAMPLE 5

Substantially the same procedures as in Example 4 were repeated except that the use of 8 g of β-cyclodextrin was omitted.

After completion of the reaction, the reaction mixture was subjected to extractions each with 50 ml of chloroform 5 times. The chloroform layer was dried to obtain 0.31 g of a product. The product thus obtained was a mixture of 28% of 4-dichloromethyl-4-methyl-2,5-cyclohexadienone, and 72% of 2-formyl-4-methylphenol. Namely, the yield of the intended product was 5% and the selectivity was 28%.

EXAMPLE 5

Substantially the same procedures as in Example 4 were repeated except that 1 g of 4-phenylphenol was used instead of 1 g of p-cresol. There was obtained 0.85 g of a product. The $^1$H-NMR measurement showed that 95% of the product was 4-dichloromethyl-4-phenyl-2,5-cyclohexadienone and the balance was 2-formly-4-phenylphenol. Namely, the yield of the intended product was 57% and the selectivity was 95%.

COMPARATIVE EXAMPLE 6

Substantially the same procedures as in Comparative Example 5 were repeated except that 1 g of 4-phenylphenol was used instead of 1 g of p-cresol. There was obtained 0.52 g of a product. The product was a mixture of 13% of 4-dichloromethyl-4-phenyl-2,5-cyclohexadienone and 87% of 2-formyl-4-phenylphenol. Namely, the yield of the intended product was 4% and the selectivity was 13%.

EXAMPLE 6

Substantially the same procedures as in Example 4 were repeated except that 1 g of 3,4,5-trimethylphenol was used instead of 1 g of p-cresol. There was obtained 0.86 g of a product. The product thus obtained was entirely 3,4,5-trimethyl-4-dichloromethyl-2,5-cyclohexadienone. Namely, the yield of the intended product was 54% and the selectivity was 100%.

COMPARATIVE EXAMPLE 7

Substantially the same procedures as in Comparative Example 5 were repeated except that 1 g of 3,4,5-trimethylphenol was used instead of 1 g of p-cresol. There was obtained 0.39 g of a product. The product thus obtained was a mixture of 7% of 3,4,5-trimethyl-4-dichloromethyl-2,5-cyclohexadienone and 93% of 3,4,5-trimethyl-2-formylphenol. Namely, the yield of the intended product was 1% and the selectivity was 7%.

EXAMPLE 7

Substantially the same procedures as in Example 4 were repeated except that 1 g of ar-2-tetrahydronaphthol was used instead of 1 g of p-cresol. There was obtained 0.50 g of 9-dichloromethyl-6-oxo-1,2,3,4,6,9-hexahydronaphthalene. Namely, the yield of the intended product was 32% and the selectivity was 100%.

COMPARATIVE EXAMPLE 8

Substantially the same procedures as in Comparative Example 5 were repeated except that 1 g of ar-2-tetrahydronaphthol was used instead of 1 g of p-cresol. There was obtained 0.54 g of a product. The product thus obtained was a mixture of 18% of 9-dichloromethyl-6-oxo-1,2,3,4,6,9-hexahydronaphthalene and 81% of 1-formyl-ar-2-tetrahydronaphthol. Namely, the yield of the intended product was 6% and the selectivity was 18%.

EXAMPLE 8

Substantially the same procedures as in Example 4 were repeated except that 1 g of 2,4,6-trimethylphenol was used instead of 1 g of p-cresol. There was obtained 0.67 g of 2,4,6-trimethyl-4-dichloromethyl-2,5-cyclohexadienone. Namely, the yield of the intended product was 42% and the selectivity was 100%.

EXAMPLE 9

Substantially the same procedures as in Example 4 were repeated except that 1 g of p-methoxyphenol was used instead of 1 g of p-cresol. There was obtained 0.26 g of a product. The product thus obtained was a mixture of 96% of 4-dichloromethyl-4-methoxy-2,5-cyclohexadienone and 4% of 2-formyl-4-methoxyphenol. Namely, the yield of the intended product was 23% and the selectivity was 96%.

EXAMPLE 10

Substantially the same procedures as in Example 7 were repeated except that 8 g of α-cyclodextrin was used instead of 8 g of β-cyclodextrin. From 1 g of ar-2-tetrahydronaphthol, there was obtained 0.38 g of a product. The product contained 9-dichloromethyl-6-oxo-1,2,3,4,6,9-hexahydronaphthalene in an amount of 93%. Namely, the yield of the intended product was 22% and the selectivity was 93%.

EXAMPLE 11

Substantially the same procedures as in Example 4 were repeated except that an aqueous 10% potassium hydroxide solution was used instead of an aqueous 10% sodium hydroxide solution. From 1 g of p-cresol, there was obtained 0.47 g of 4-dichloromethyl-4-methyl-2,5-cyclohexadienone. Namely, the yield of the intended product was 26% and the selectivity was 100%.

What is claimed is:

1. In a process for producing a para-substituted phenol derivative which comprises reacting a phenol compound represented by the formula (I)

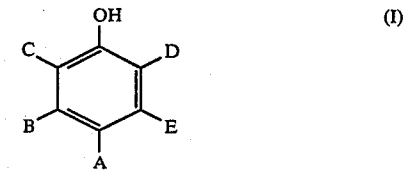

wherein A, B, C, D and E each independently stand for hydrogen, a hydroxyl group, a substituted or unsubstituted alkyl group, a substituted or unsubstituted allyl group, a substituted or unsubstituted alkoxyl group or a substituted or unsubstituted aryl group, provided that A does not stand for a hydroxyl group and that when two or more of A, B, C, D, and E each independently stand for a substituted or unsubstituted alkyl group or a substituted or unsubstituted alkoxyl group, they have their respective free terminal ends or at least one of them is bonded to another group selected from said alkyl and alkoxyl groups to form a ring, with a haloform in the presence of an alakli metal hydroxide, using as a catalyst a modified or unmodified cyclodextrin, thereby to introduce an aldehyde group or a dihalomethyl group derived from said haloform to the para-position of the phenol compound, the improvement wherein the reaction is effected while maintaining the molar ratio of said modified or unmodified cyclodextrin to said haloform at 0.5 to 10.

2. A process according to claim 1, wherein said substituted or unsubstituted alkyl group, said substituted or unsubstituted allyl group, said substituted or unsubstituted alkoxyl group and said substituted or unsubstituted aryl group each have carbon atoms of not more than 6 with respect to B, C, D and E and each have carbon atoms of not more than 12 with respect to A.

3. A process according to claim 1, wherein said alkali metal hydroxide is sodium hydroxide or potassium hydroxide.

4. A process according to claim 1, wherein said alkali metal hydroxide is employed in an amount of 1 to 15 times the stoichiometrical amount of said alkali metal hydroxide relative to said phenol compound.

5. A process according to claim 1, wherein said organic halide is employed in an amount of 1 to 20 in term of molar ratio with respect to said phenol compound.

6. A process according to claim 1, wherein the reaction is effected while maintaining the molar ratio of said modified or unmodified cyclodextrin to said haloform at 0.8 to 5.

7. A process according to claim 1, wherein the reaction is effected by intermittently or gradually adding the haloform to a system comprising the phenol compound, the alkali metal hydroxide and the modified or unmodified cyclodextrin.

8. A process according to claim 1, wherein the reaction is effected at 0° to 120° C.

9. A process according to claim 1, wherein the reaction is effected in an aqueous medium.

10. A process according to claim 1, wherein A in the formula(I) is hydrogen and said para-substituted phenol derivative is represented by the formula(II)

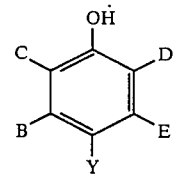

wherein B, C, D and E are as defined above and Y stands for an aldehyde group, or A in the formula(I) is a substituted or unsubstituted alkyl group, a substituted or unsubstituted allyl group, a substituted or unsubstituted alkoxyl group or a substituted or unsubstituted aryl group and said para-substituted phenol derivative is represented by the formula(III)

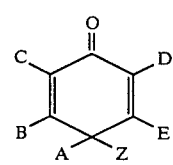

wherein A, B, C, D and E are as defined above, provided that A does not stand for hydrogen, and Z stands for a haloform residue.

* * * * *